(12) United States Patent
Ferguson

(10) Patent No.: US 11,147,648 B2
(45) Date of Patent: Oct. 19, 2021

(54) HEADLAMP ASSEMBLY HAVING COMFORT ELEMENT

(71) Applicant: RIVERPOINT MEDICAL, LLC, Portland, OR (US)

(72) Inventor: John Thomas Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 52 days.

(21) Appl. No.: 16/255,277

(22) Filed: Jan. 23, 2019

(65) Prior Publication Data

US 2020/0229891 A1 Jul. 23, 2020

(51) Int. Cl.
| | | |
|---|---|---|
| *A61B 90/30* | (2016.01) |
| *A61B 90/35* | (2016.01) |
| *F21V 21/084* | (2006.01) |
| *A61B 90/50* | (2016.01) |
| *F21W 131/20* | (2006.01) |

(52) U.S. Cl.
CPC ............ *A61B 90/35* (2016.02); *F21V 21/084* (2013.01); *A61B 2090/502* (2016.02); *F21W 2131/20* (2013.01)

(58) Field of Classification Search
CPC .... F21V 21/084; F21V 33/0068; F21V 15/00; F21Y 2101/00; A61B 1/06; A61B 19/5202; A61B 19/262; A61B 2019/521; A61B 2019/084; A61B 2019/262; A42B 1/242

See application file for complete search history.

(56) References Cited

U.S. PATENT DOCUMENTS

| | | | | |
|---|---|---|---|---|
| 8,348,448 | B2* | 1/2013 | Orozco | A61B 1/0692 362/105 |
| 9,351,799 | B2* | 5/2016 | Ferguson | B29C 70/72 |
| 2009/0154143 | A1* | 6/2009 | Heine | F21L 4/00 362/105 |
| 2010/0095438 | A1* | 4/2010 | Moelker | A42B 1/22 2/418 |
| 2012/0120635 | A1* | 5/2012 | Strong | A61B 90/53 362/105 |
| 2014/0226264 | A1* | 8/2014 | Davidson | F21V 21/088 361/679.01 |

(Continued)

*Primary Examiner* — Eduardo C Robert
*Assistant Examiner* — Steven J Cotroneo
(74) *Attorney, Agent, or Firm* — Timothy E. Siegel Patent Law, PLLC; Timothy E. Siegel

(57) ABSTRACT

A medical headlamp headband assembly, having a preferred orientation relative to a wearer's head, and comprising a closed form headband, adapted to encircle a human head horizontally, thereby defining a head-facing side and having a tightness adjustment feature in a rear central location relative to a wearer's head when the headband assembly is worn in its preferred orientation. A tightness adjustment subassembly, at a central rear location, is opposed to the front location. A resiliently deformable wing-set is supported by the headstrap subassembly on the head-facing side, about the tightness adjustment subassembly and including a central part and two wings, each extending laterally outwardly from the central part. Each wing extends forward as it extends laterally from the central part, to contact the wearer's head at a rear side location, thereby holding the tightness adjustment assembly back from the wearer's head.

7 Claims, 5 Drawing Sheets

(56) References Cited

U.S. PATENT DOCUMENTS

2017/0211759 A1* 7/2017 Qiu .......................... F21L 4/04
2018/0306418 A1* 10/2018 Koyama ............... F21V 21/084
2019/0298479 A1* 10/2019 Eddy .................... F21V 21/084
2020/0003400 A1* 1/2020 Kelly ....................... F21L 4/00
2020/0109847 A1* 4/2020 Poggio .................. A61B 90/30

* cited by examiner

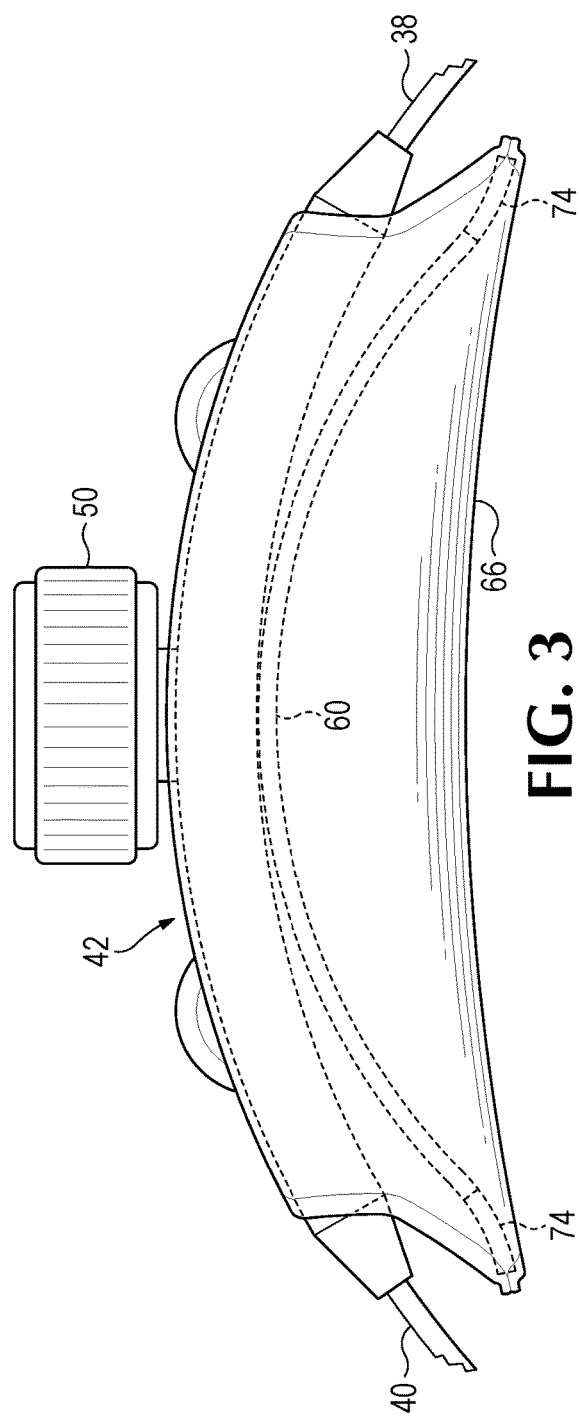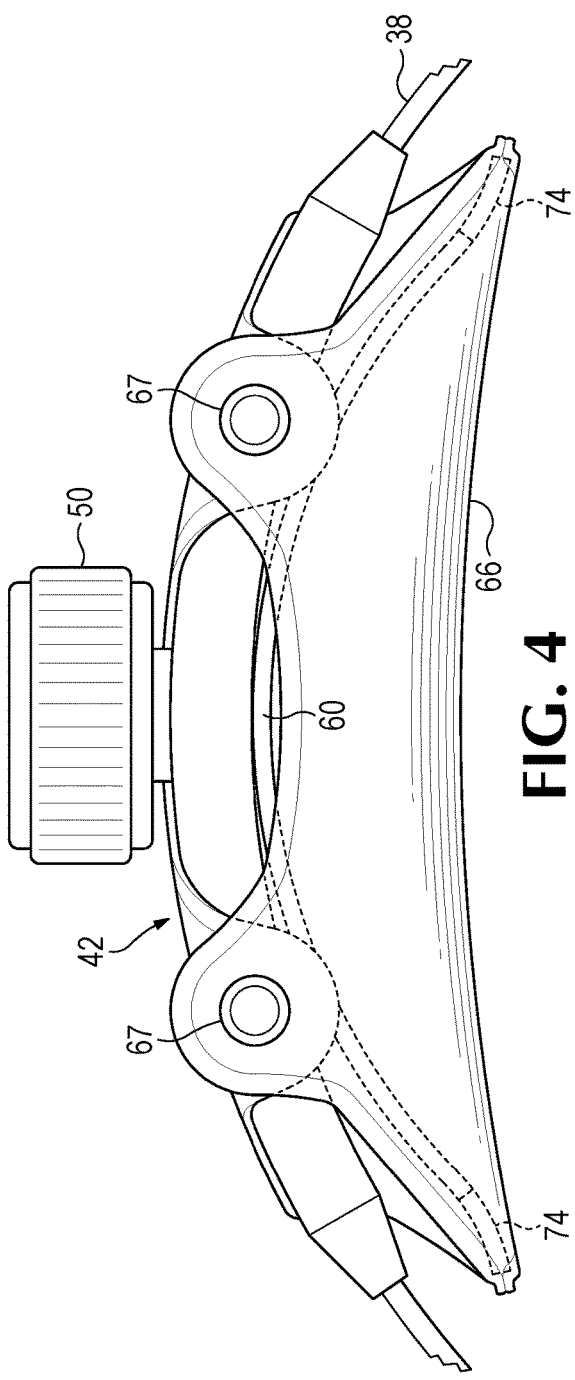

HEADLAMP ASSEMBLY HAVING COMFORT ELEMENT

BACKGROUND OF THE INVENTION

An item that is worn, even if comfortable at first, can become painfully uncomfortable after a few hours. This is certainly the case with the headband for a medical headlamp assembly. In order to keep the headlamp rigidly in place, the headband must have some rigidity and must be fastened firmly to the head. But this means that any incongruity between the strap, which is essentially flat, and the sides of the head of the wearer, which are not flat, will become increasingly painful over time. Although many headstrap configurations have been used over the years, none appear to have been fully embraced by the community of surgeons using them. Some further innovation is desirable.

One device intended to ease the sensation of wearing a medical headlamp for a long period of time is described in U.S. Pat. No. 8,348,448. The "stabilizer" described in this patent, however, may prove a burden to some wearers, due to its size. In particular, wearers with long hair, in particular, if it is arranged in a pony tail, may be faced with a difficulty in threading their hair through the headband, as it may be blocked by the stabilizer.

SUMMARY OF INVENTION

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements.

A medical headlamp headband assembly, having a preferred orientation relative to a wearer's head, and comprising a closed form headband, adapted to encircle a human head horizontally, thereby defining a head-facing side and having a tightness adjustment feature in a rear central location relative to a wearer's head when the headband assembly is worn in its preferred orientation. A tightness adjustment subassembly, at a central rear location, is opposed to the front location. A resiliently deformable wing-set is supported by the headstrap subassembly on the head-facing side, about the tightness adjustment subassembly and including a central part and two wings, each extending laterally outwardly from the central part. Each wing extends forward as it extends laterally from the central part, to contact the wearer's head at a rear side location, thereby holding the tightness adjustment assembly back from the wearer's head.

A medical headlamp headband assembly, having a preferred orientation relative to a wearer's head, and having a closed form headband, adapted to encircle a human head horizontally. A top strap is configured to extend over the head of a wearer, thereby defining a head-facing side and including a top strap tightness adjustment subassembly. Further, a resiliently deformable wing-set is supported by the top strap on the head-facing side, about the tightness adjustment subassembly and including a central part and two wings, each extending laterally outwardly from the central part and being vertically coincident to the top strap. Further, each wing extends downward as it extends laterally from the central part, to contact the wearer's head at a top side location, thereby holding the tightness adjustment assembly away from the wearer's head.

A method of illuminating a surgeon's field of view, that uses a medical headlamp assembly including a headstrap, a linkage supported by the headstrap and a headlamp, supported by the linkage. The headstrap includes a closed form headband, adapted to encircle a human head horizontally, thereby defining a head-facing side and having a tightness adjustment feature in a rear central location relative to a wearer's head when the headband assembly is worn in its preferred orientation. A tightness adjustment subassembly, is present a central rear location, opposed to the front location. Further, a resiliently deformable wing-set, having a central portion supported by the headstrap subassembly on the head-facing side, about the tightness adjustment subassembly and further having two wings, each wing extending laterally outwardly from the central part, each wing extending forward as it extends laterally from the central part. The headstrap is placed on the surgeon's head, oriented so that the headlamp is positioned at a midpoint on the surgeon's forehead, and wherein each wing presses against a back-side area of the surgeon's head, thereby lifting the tightness adjustment sub-assembly away from the back of the surgeon's head. The headlamp is activated to illuminate the surgeon's field of view.

A medical headlamp headband assembly, comprising a closed form headband, adapted to encircle a human head, and having a tightness adjustment feature and a pair of top band attachment elements. A first top band is made of a first material and includes two flexible longitudinal portions that are engaged together, and that can be tightened or loosened by increasing or decreasing overlap between the portions, and has two ends, both of which terminate in a headband attachment element that is engageable to the top band attachment element. A second top band comprises material that is softer and more flexible than the first material respectively, the second top band having two ends, both of which are engageable to the top band attachment element. A user can pick either the first top band or the second top band and attach it to the closed form headband.

BRIEF DESCRIPTION OF DRAWINGS

Various embodiments of the invention are disclosed in the following detailed description and accompanying drawings.

FIG. 3 is a top view of a wing set attachment of FIG. 2, in an assembled state about a tightening adjustment mechanism of the headlamp of FIG. 1.

FIG. 4 is a bottom view of a wing set attachment of FIG. 2, in an assembled state about a tightening adjustment mechanism of the headlamp of FIG. 1.

DETAILED DESCRIPTION AND EMBODIMENTS

The following is a detailed description of exemplary embodiments to illustrate the principles of the invention.

The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

To assist the description of the scope and its components the coordinate terms ["proximal" and "distal"] are used to describe the disclosed embodiments. The terms are used consistently with the description of the exemplary applications and are in reference to [the head of a user]. In other words, [proximal components are nearer to the user than distal components].

1. Definitions

The term "strap" as used in this application may refer to two straps joined together by an adjustable joining element, such as a buckle.

2. Description

Figure 1:
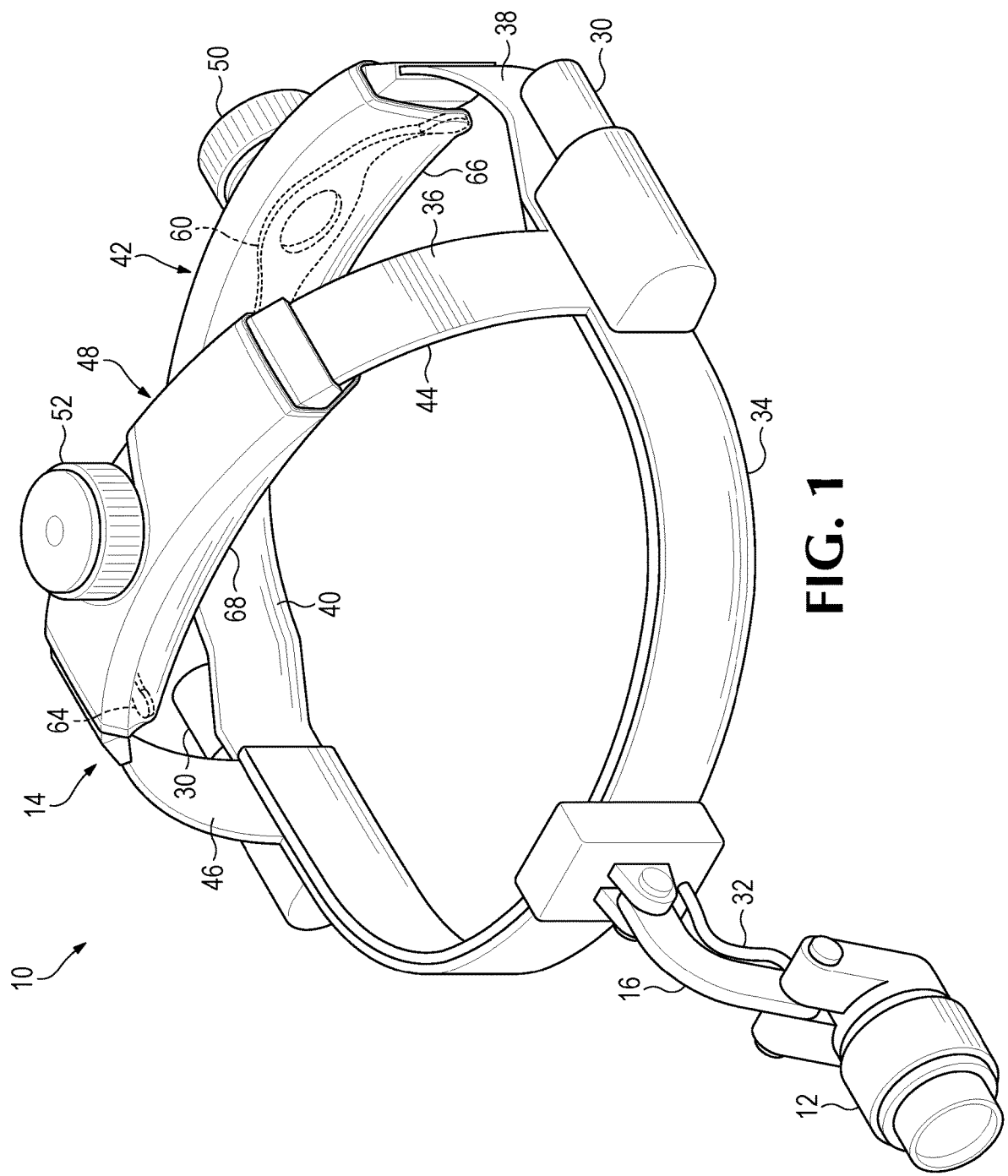
FIG. 1 is an isometric view of a headlamp assembly, according to the present invention.
Figure 5:
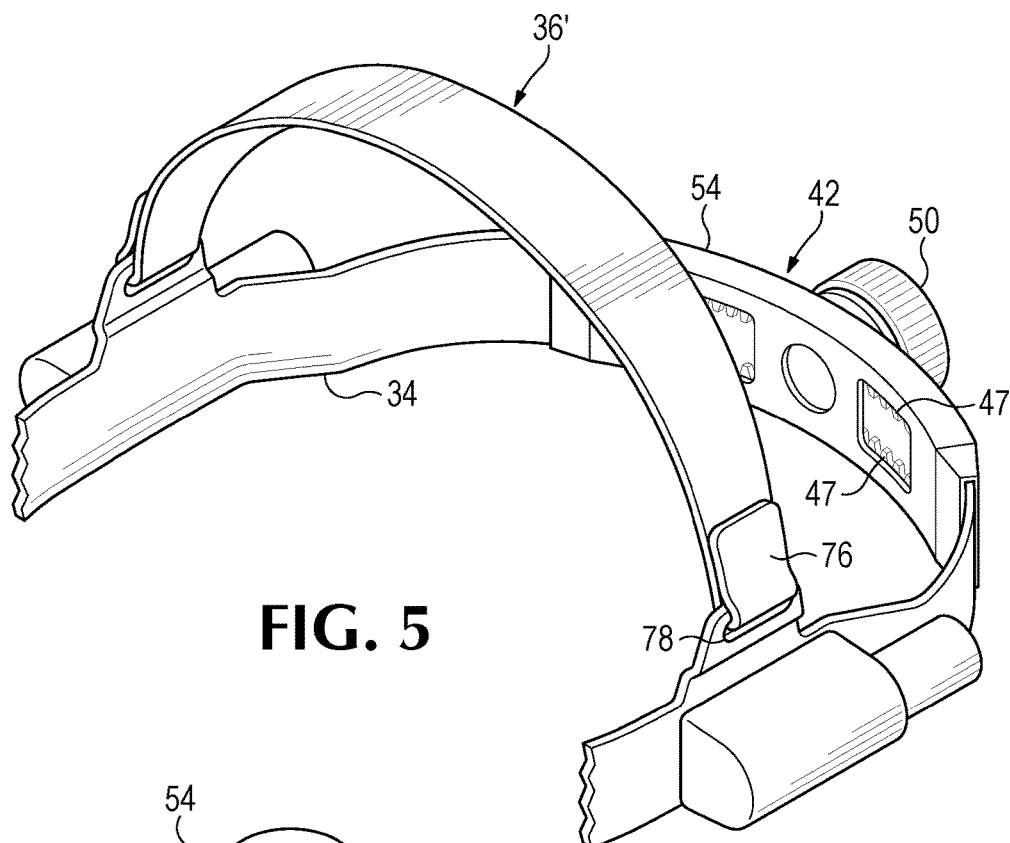
FIG. 5 is a partial perspective view of an alternative embodiment of the headlamp assembly of FIG. 1, showing a soft top strap placed into use.
Figure 6:
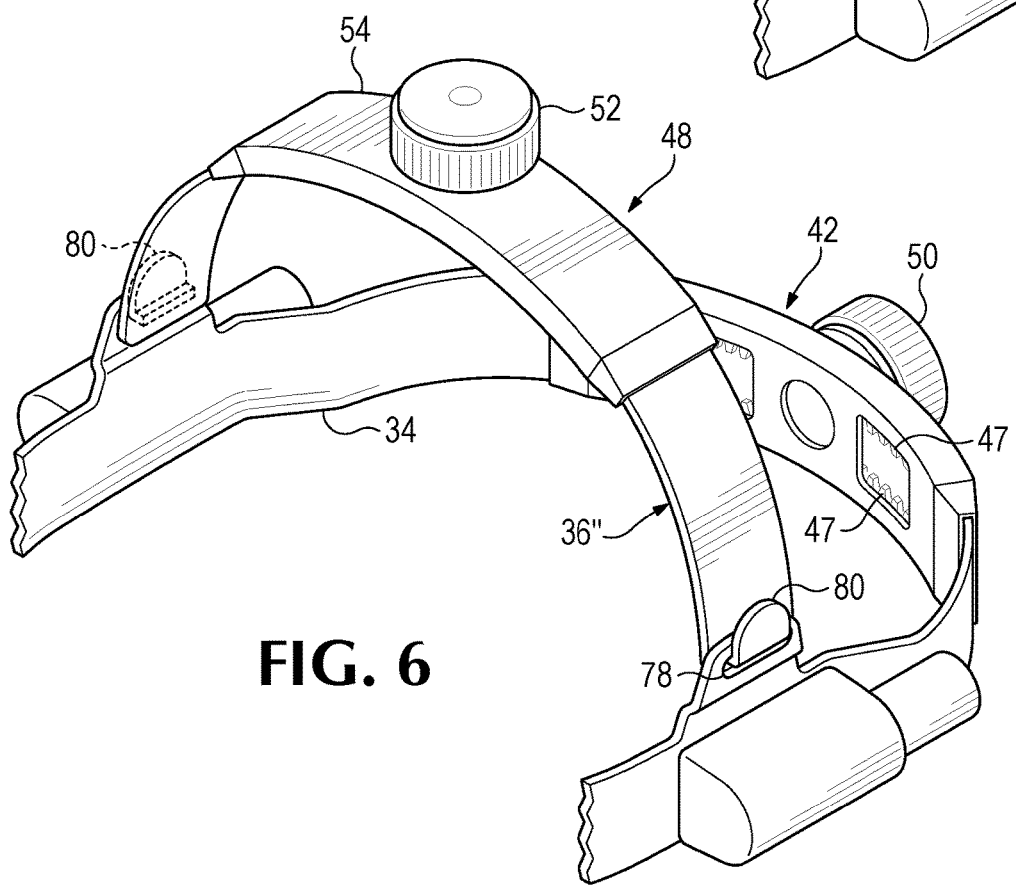
FIG. 6 is a partial perspective view of the alternative embodiment of FIG. 5, showing a tightness adjustable top strap placed into use.

Referring to FIG. 1, in a preferred embodiment, a medical headlamp assembly 10 includes a headlamp (also known as a bezel) 12, a headband assembly 14, and a linkage 16, supporting the headlamp 12 from the headband assembly 14. Batteries 30 supply electric power to headlamp 12, typically through an electrical network (not shown) housed in headband assembly 14, and a final wire 32 or other, similar, electrical conductor. Headband assembly 14 is made of a headband 34 and a top band 36. Headband 34 is made up of two straps 38 and 40 that are joined together by tightening mechanism 42. Similarly, the top band 36 is made up of two straps 44 and 46 that are joined together by tightening mechanism 48. Referring to FIGS. 5 and 6, both strap 38 and strap 40 have a an opening with teeth 47 on the top (for a first one of strap 38 and 40), or on the bottom (for a second one of strap 38 or 40), so that a cog wheel (not shown) affixed to a knob 50, will pull straps 38 and 40 to greater overlap with each other when turned in a first direction, and to less overlap with each other when turned in a second direction, opposite to the first direction. An identical mechanism works for a knob 52 and straps 44 and 46 of top strap 36. This mechanism represents a great convenience to a surgeon preparing for a surgery, but the need for teeth 47 means that harder polymer materials must be used for straps 38, 40, 44 and 46 than would otherwise be needed. Also, the use of cog wheels (not shown) and guide/holders 54 to keep teeth 47 aligned, make tightening mechanisms 42 and 48 harder than other parts of straps 34 and 36, resulting in discomfort for extended wear.

Wing-sets 60 and 64 are made of a soft, resiliently deformable material such as nylon, polyester a thin strip of resiliently deformable metal, or some combination of these materials. Mechanisms 42 and 48, and the surfaces of the human head do not perfectly conform. Accordingly, it is more comfortable if mechanisms 42 and 48 are kept suspended away from the surfaces of the head, as is done by the two wings of both wing-set 60 and 64. The ears 74 of wing-sets 60 and 64 gently contact the head (through a layer of fabric, as explained below), avoiding the irritating pressure of a harder contact. Each wing set 60 and 64, includes a central hole 70, which in one embodiment connects about a matching protrusion in the head-facing surface of mechanisms 42 and 48.

Figure 2:
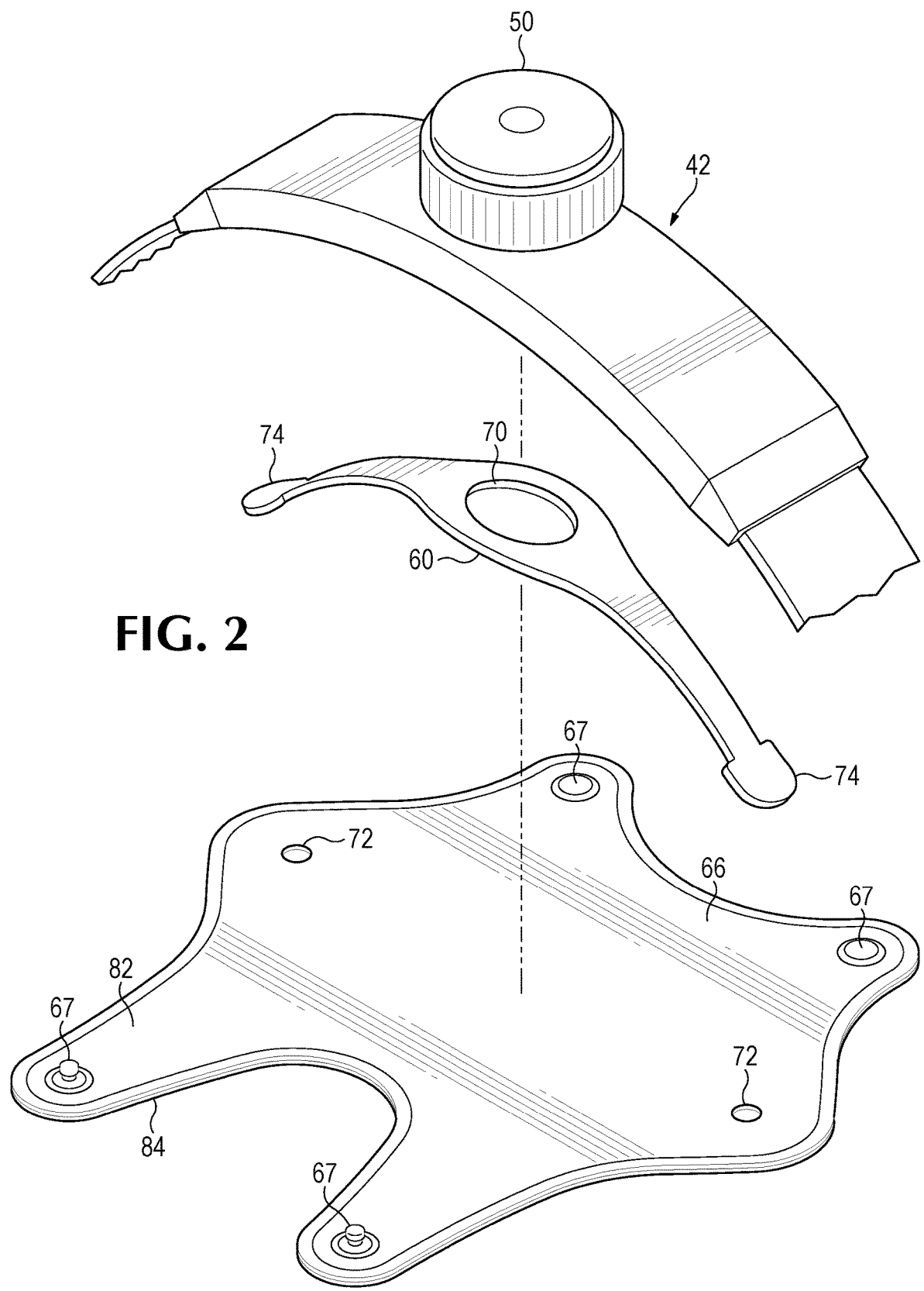
FIG. 2 is a view showing the back wing set attachment of the headlamp assembly of FIG. 1, in a disassembled state (and rotated 90°, to vertical).
Figure 2A:
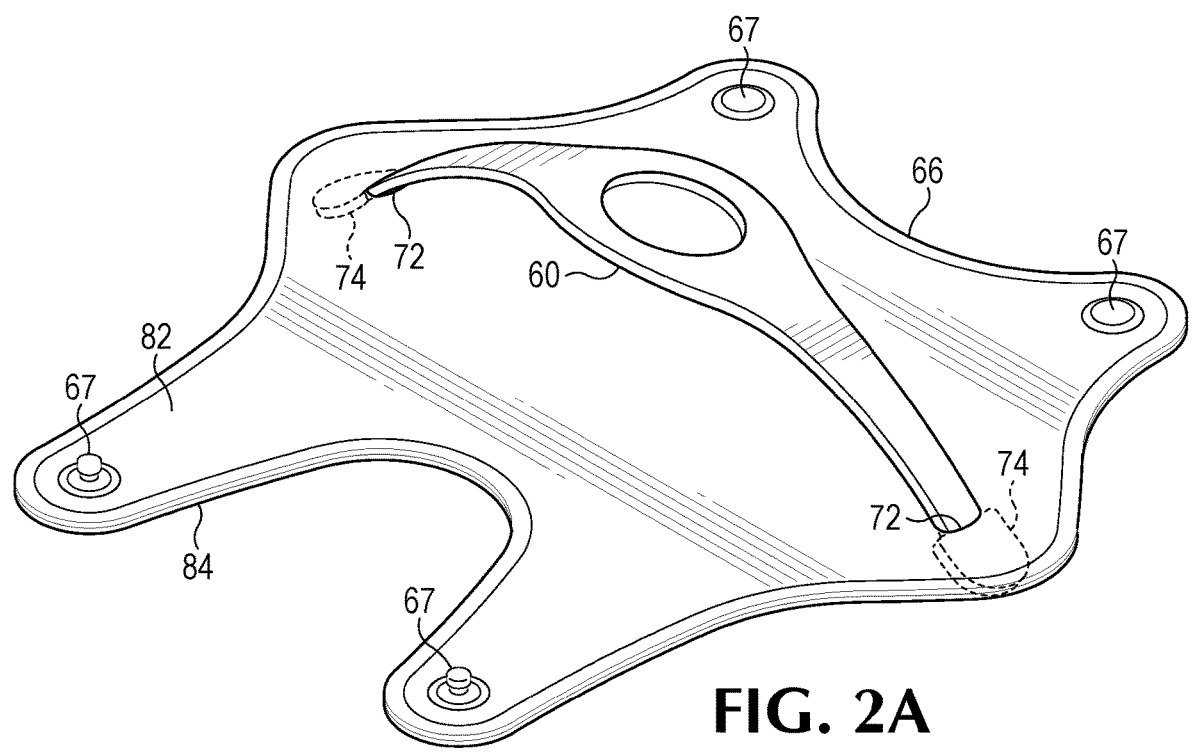
FIG. 2A is a view showing the back wing set attachment of FIG. 2, in an assembled state.

Wing set 60 is held in place by rear wing-set holder 66, which snaps together wrapped about wing set 60 and mechanism 42. In like manner top wing-set 64 is held in place by a top wing-set holder 68. In one embodiment wraps 66 and 68 are made of quilted material. In another embodiment they are made of polypropylene. For both wraps 66 and 68, side holes 72, receive ears 74 of wing set 60 and 64, respectively. This results in ears 74 being cushioned against the side/back of a user's head by a layer of material and of positively retaining ears 74 and thereby, wing sets 60 and 64, with a wrap 66 and 68. Referring now to FIG. 2A, the wing set holder 66 is made of two sheets of material 82 and 84 joined together, with sheet 82 defining a pair of through-holes 72, through which ears 74 pass, whereby the wing set 60 and the wing set holder 66 are mutually retained in place.

Referring to FIGS. 5 and 6, in another aspect of a preferred embodiment a pair of alternative top bands, 36' and 36" are provided. Referring to FIG. 5, top band 36' is soft and elastic, making it more comfortable for many users, and is attachable by way of hook and loop material (not shown), that permits band 36' to form a loop through a slot 78 defined in headband 34. Referring specifically to FIG. 6, top band 36" is the same as band 36, except for that it can be disengaged from headband 34, by removing hooks 80 from slots 78. As some users prefer top band 36' and others prefer top band 36" distribution can be eased by providing each purchaser with both, but they must be made interchangeable, to be able to do this. In an alternative preferred embodiment, a top band similar to 36" is provided, but wherein instead of hooks 80, the top band attaches to itself, forming a loop for engagement to band 34, by means of mating hook and loop material.

The disclosed embodiments may be used to illuminate a field of view of a surgeon. The surgeon may place assembly 10 on his head, with the headlamp 12 projecting forward from the center of his or her forehead. Tightness adjustments may be made using knobs 50 and 52. But tightness adjustment mechanisms 42 and 48 are lifted away from the surgeon's head by wing sets 60 and 64, respectively. Accordingly, as headlamp 12 illuminates the surgeon's field of view, the surgeon may be more comfortable in assembly 10, than he could otherwise be.

3. Statement Regarding Scope

The disclosed embodiments are illustrative, not restrictive. While specific configurations of the headlamp assembly design have been described, it is understood that the present invention can be applied to a wide variety of headband uses. There are many alternative ways of implementing the invention.

What is claimed is:

1. A medical headlamp headband assembly, having a preferred orientation relative to a wearer's head, and comprising:
 a) a closed form headband, adapted to encircle a human head horizontally, thereby defining a head-facing side and having a tightness adjustment feature in a rear central location relative to a wearer's head when said headband assembly is worn in its preferred orientation;
 b) a resiliently deformable wing-set, supported by said headband on said head-facing side, about said tightness adjustment feature and including a central part and two wings, each extending laterally outwardly from said central part, each wing extending forward as it extends laterally from said central part, to contact said wearer's head at a rear side location, thereby holding said tightness adjustment feature back from said wearer's head, each said wing having a pair termini at either lateral furthest extent; and c) a wing set holder that is, in part, engaged to and suspended between said termini, so that there is a gap between a part of said holder and said central part of said wing-set, said wing set contacting said wearer's head through said wing set holder;

d) wherein said wing set is held in place on said tightness adjustment feature by said wing set holder, which is joined to itself, to form a loop about said wing set and said tightness adjustment feature; and e) wherein said wing set holder is made of two sheets of material joined together, and wherein a first one of said two sheets of material defines a first through-hole, through which a portion of a first one of said wings passes, and a second through-hole through which a portion of a second one of said wings passes, whereby said wing set and said wing set holder are mutually retained in place.

2. The medical headlamp assembly of claim 1, wherein said tightness adjustment feature is more rigid than other portions of said headband, thereby potentially causing discomfort.

3. The medical headlamp assembly of claim 1, wherein said wing set is a rear wing set and wherein said headband further includes a top strap assembly that is joined to said headband at two opposed locations, and is configured to extend over the top of a wearer's head, and includes a top tightness adjust assembly, and wherein a top resiliently deformable wing set is located about said top tightness adjust assembly and includes a central portion and a pair of wings projecting outwardly and downwardly from about said top tightness adjust assembly, to hold said top tightness adjust assembly away from a wearer's head.

4. The medical headlamp assembly of claim 3, further including a rear wing set holder which is joined together about said rear wing set and said tightness adjust feature, to hold said rear wing set in place, and further including a top wing set holder that is joined together about said top wing set and said top tightness adjust mechanism, to hold said top wing set in place.

5. The medical headlamp assembly of claim 1, wherein wing set holder is joined to itself, by being snapped to itself, using opposed snaps.

6. A medical headlamp headband assembly, having a preferred orientation relative to a wearer's head, and comprising:

a) a closed form headband, adapted to encircle a human head horizontally, b) a top strap configured to extend over the head of a wearer, thereby defining a head-facing side and including a top strap tightness adjustment subassembly;

c) a resiliently deformable wing-set, supported by said top strap on said head-facing side, about said tightness adjustment subassembly and including a central part and two wings, each extending laterally outwardly from said central part and horizontally coincident to said top strap, each wing extending downward as it extends laterally from said central part, to contact said wearer's head at a top side location, thereby holding said tightness adjustment assembly away from said wearer's head, each said wing having a pair termini at either lateral furthest extent; and d) a wing set holder that is, in part, suspended between said termini, so that there is a gap between a part of said holder and said central part of said wing-set, said wing set contacting said wearer's head through said wing set holder;

e) wherein said wing set is held in place on said tightness adjustment mechanism by said wing set holder, which is joined to itself, to form a loop about said wing set and said tightness adjustment assembly; and f) wherein said wing set holder is made of two sheets of material joined together, and wherein a first one of said two sheets of material defines a first through-hole, through which a portion of a first one of said wings passes, and a second through-hole through which a portion of a second one of said wings passes, whereby said wing set and said wing set holder are mutually retained in place.

7. The medical headlamp assembly of claim 6, wherein wing set holder is joined to itself, by being snapped to itself, using opposed snaps.

* * * * *